(12) United States Patent
Bague et al.

(10) Patent No.: US 8,372,434 B2
(45) Date of Patent: Feb. 12, 2013

(54) OPHTHALMIC OIL-IN-WATER TYPE EMULSION WITH STABLE POSITIVE ZETA POTENTIAL

(75) Inventors: Séverine Bague, Epinay sur Orge (FR); Betty Philips, Antony (FR); Laura Rabinovich-Guilatt, Kadima (IL); Gregory Lambert, Chatenay Malabry (FR); Jean-Sébastien Garrigue, Verrieres le Buisson (FR)

(73) Assignee: Novagali Pharma SA, Evry (FR)

( * ) Notice: Subject to any disclaimer, the term of this patent is extended or adjusted under 35 U.S.C. 154(b) by 1131 days.

(21) Appl. No.: 11/667,355

(22) PCT Filed: Oct. 10, 2005

(86) PCT No.: PCT/EP2005/011650
§ 371 (c)(1),
(2), (4) Date: May 9, 2007

(87) PCT Pub. No.: WO2006/050838
PCT Pub. Date: May 18, 2006

(65) Prior Publication Data
US 2007/0248645 A1 Oct. 25, 2007

(30) Foreign Application Priority Data

Nov. 9, 2004 (EP) .................................... 04292645

(51) Int. Cl.
*A61K 9/14* (2006.01)
*A61F 2/00* (2006.01)
*C07C 231/00* (2006.01)

(52) U.S. Cl. ........................... 424/489; 514/954; 554/52
(58) Field of Classification Search .................. 424/489; 514/954; 554/52
See application file for complete search history.

(56) References Cited

U.S. PATENT DOCUMENTS

| | | | | |
|---|---|---|---|---|
| 5,496,811 A | * | 3/1996 | Aviv et al. ........................ | 514/78 |
| 5,588,559 A | * | 12/1996 | Vallet Mas et al. ............. | 222/92 |
| 5,698,219 A | * | 12/1997 | Valdivia et al. ................ | 424/450 |
| 6,007,826 A | | 12/1999 | Benita et al. | |
| 6,656,460 B2 | | 12/2003 | Benita et al. | |
| 6,872,705 B2 | * | 3/2005 | Lyons ............................ | 514/2.3 |
| 2003/0108626 A1 | | 6/2003 | Benita et al. | |
| 2005/0059583 A1 | * | 3/2005 | Acheampong et al. ......... | 514/11 |
| 2005/0175651 A1 | * | 8/2005 | Simonnet et al. ............. | 424/401 |
| 2006/0257426 A1 | * | 11/2006 | Baker et al. ................. | 424/204.1 |

FOREIGN PATENT DOCUMENTS

| | | |
|---|---|---|
| EP | 0 696 452 A | 2/1996 |
| EP | 0 878 197 A | 11/1998 |
| EP | 1 611 879 A | 1/2006 |
| WO | 03/053405 A | 7/2003 |

OTHER PUBLICATIONS

Benzyl Dimethyl Hexadecyl Ammonium Chloride, poroduct indentification, synonyms, [online Aug. 13, 2010], Retrieved from URL:<http://chemicalland21.com/specialtychem/perchem/BENZYL%20DIMETHYL%20HEXADECYL%20AMMONIUM%20CHLORIDE.htm>.*
Klang et al., Influence of Emulsion Droplet Surface Charge on Indomethacin Ocular Tissue Distribution, 2000, Pharmaceutical Development and Technology, vol. 5, No. 4, pp. 521-532.*
Choi, W-J et al., "Low Toxicity of Cationic Lipid-Based Emulsion for Gene Transfer", Biomaterials, Feb. 25, 2004, pp. 5893-5903, vol. 25, No. 27, Elsevier Science Publishers B.V., Barking, GB.
Ott, G. et al., "A Cationic Sub-Micron Emulsion (MF59/DOTAP) Is an Effective Delivery System for DNA Vaccines", Journal of Controlled Release, Feb. 19, 2002, pp. 1-5, vol. 79, No. 1-3, Elsevier Science Publishers BV., Amsterdam, NL.
Ogawa, S. et al., "Production and Characterization of O/W Emulsions Containing Cationic Droplets Stabilized by Lecithin-Chitosan Membranes", Journal of Agricultural and Food Chemistry, Apr. 23, 2003, pp. 2806-2812, vol. 51, No. 9, American Chemical Society.
Tamilvanan, S. et al., "The Potential of Lipid Emulsion for Ocular Delivery of Lipophilic Drugs", European Journal of Pharmaceutics, Jun. 1, 2004, pp. 357-368, vol. 58, No. 2, Elsevier Science Publishers BV., Amsterdam, NL.
English Language Abstract of Klang, S. et al., "Influence of Emulsion Droplet Surface Charge on Indomethacin Ocular Tissue Distribution", Pharm. Dev. Technology, 2000, vol. 5, pp. 521-532.
Washington, C., "Stability of Lipid Emulsions for Drug Delivery", Advanced Drug Delivery Reviews, 1996, vol. 20, pp. 131-145, Elsevier Science Publishers B.V.
Rabinovich-Guilatt, L. et al., "Extensive Surface Studies Help to Analyse Zeta Potential Data: The Case of Cationic Emulsions", Chemistry and Physics of Lipids, 2004, vol. 131, 1-13, Elsevier Ireland Ltd.
English Language Abstract of Liu, F. et al., "New Cationic Lipid Formulations for Gene Transfer", Pharm Res., 1996, vol. 13, pp. 1856-1860.
Klang, S. et al., "The Stability of Piroxicam Incorporated in a Positively-Charged Submicron Emulsion for Ocular Administration", International Journal of Pharmaceutics, 1996, vol. 132, pp. 33-44, Elsevier Science Publishers B.V.
English Language Abstract of Zuidam, N.J. et al., "Chemical Hydrolysis of Phospholipids", J Pharm Sci., 1996, vol. 84, pp. 1113-1119.

(Continued)

*Primary Examiner* — Lezah Roberts
*Assistant Examiner* — Nannette Holloman
(74) *Attorney, Agent, or Firm* — Young & Thompson

(57) ABSTRACT

An ophthalmic oil-in-water type emulsion, which includes colloid particles having an oily core surrounded by an interfacial film, the emulsion including at least one cationic agent, at least one no ionic surfactant, the emulsion having a positive zeta potential and meeting zeta potential stability Test A requirements. Process for making the emulsions. Delivery device selected from the group including lenses, ocular patch, implant, insert, the device containing an emulsion according to the invention.

19 Claims, No Drawings

OTHER PUBLICATIONS

Varveri, F.S. et al., "Chemiluminescence Monitoring of Hemolysis by Lysophospholipids", Journal of Photochemistry and Photobiology A, 1995, vol. 91, pp. 121-124, Elsevier Science S.A.

Tamilvanan, S. et al., "Ocular Delivery of Cyclosporin A 1. Design and Characterization of Cyclosporin A-Loaded Positively-Charged Submicron Emulsion", S.T.P. Pharma Sciences, 2001, vol. 11, No. 6, pp. 421-426.

Jumaa, M. et al., "Physicochemical Properties of Chitson-Lipid Emulsions and Their Stability During the Autoclaving Process", International Journal of Pharmaceutics, 1999, vol. 183, pp. 175-184, Elsevier Science B.V.

Jumaa, M. et al. "A New Lipid Emulsion Formulation with High Antimicrobial Efficacy Using Chitosan", European Journal of Pharmaceutics and Biopharmaceutics, 2002, vol. 53, pp. 115-123, Elsevier Science B.V.

English Language Abstract of Klang, S.H. et al., "Physicochemical Characterization and Acute Toxicity Evaluation of a Positively-Charged Submicron Emulsion Vehicle", J. Pharm Pharmacol., 1994, vol. 46, pp. 986-993.

English Language Abstract of Furrer, P. et al., "Ocular Tolerance of Preservatives and Alternatives", Eur J Pharm Biopharm, 2002, vol. 53, pp. 263-280.

* cited by examiner

OPHTHALMIC OIL-IN-WATER TYPE EMULSION WITH STABLE POSITIVE ZETA POTENTIAL

The present invention concerns ophthalmic cationic oil-in-water type emulsions having a zeta potential remaining positive overtime.

By "ophthalmic emulsion", it is meant an emulsion which is suitable for an ocular application and which may have a pharmaceutical effect or a cosmetic effect.

Emulsions according to the invention have a zeta potential remaining positive overtime that is, they are stable overtime.

Stability is defined as the extent to which a product retains, within specified limits and throughout its period of storage and use (i.e., its shelf life), the same properties and characteristics that it possessed at the time of manufacture. The purpose of stability testing is to provide evidence on how the quality of a drug substance or drug product varies overtime under the influence of a variety of environmental factors such as temperature, humidity and light, and enables recommended storage conditions, re-test periods and shelf lives to be established.

Although real-time stability studies include an evaluation of those factors that ultimately affect the expiration date of the drugs, they are time and cost-consuming. Conventionally, accelerated stability studies are used for predicting the shelf life of pharmaceutical products. Such accelerated studies subject the systems to a temperature of 40° C. during at least 6 months.

In order to understand the intrinsic stability mechanism of the system by establishing degradation pathways and identifying the likely degradation products, and thus to adjust the analytical procedures to be used, the Applicant has developed stress stability testing during which the emulsions are subjected to extreme conditions that is a temperature of 80° C. during specified period of time.

Mathematical extrapolations, such as the Arrhenius equation, are then used to calculate the product's predicted shelf life. Application of Arrhenius equation in pharmaceutical stability testing is straightforward. In the isothermal method, the system to be investigated is stored under several high temperatures with all other conditions fixed. Excess thermal exposure accelerates the degradation and thus allows the rate constants to be determined in a shorter time period.

In recent years, oil-in-water type emulsions, in particularly emulsions having droplets of a submicron size (hereinafter "submicron emulsions") gained increasing importance, in particular as vehicles for delivery of hydrophobic drugs.

However, stabilizing emulsions, including submicron emulsions, may be a concern for one skilled in the art. One known approach to stabilize an emulsion is to confer an electrostatic charge to the droplets surface which will result in droplet repulsion and less droplet coalescence. Colloidal particles dispersed in a solution are electrically charged due to their ionic characteristics and dipole attributes. This charge, which can be negative resulting in anionic emulsions or positive producing cationic emulsions (Klang et al., Pharm. Dev. Technology 2000, 5, 521-532) is known in the art as the "zeta potential". The zeta potential is a measure of the magnitude of the repulsion or attraction between particles (Washington, Adv. Drug Deliv. Reviews 1996, 20:131-145).

Formulations of submicron emulsions reported in the literature are usually based on a combination of lecithins which are mixtures of phospholipids of various compositions obtained from natural sources, non-ionic or ionic surfactants and of oil such as vegetable oil. Lecithins generally comprise as major components phosphatidylcholine, which is neutral over a wide pH range, negatively charged phospholipids such as phosphatidylserine and phosphatidic acid and positively charged phospholipids such as phosphatidylethanolamine. As a consequence of their composition, the colloid particles in most available phospholipid-based emulsions are negatively charged. Addition of enough amounts of cationic agents such as stearylamine, oleylamine, chitosan, {N-[i-(2,3-dioleoyloxy)propyl]-N,N,N-trimethyiammonium (DOTAP) or others can reverse this surface charge and produce a positively-charged colloid, as reflected by their zeta potential (Rabinovich-Guilatt et al., Chem Phys Lipids 2004, 131:1-13; Liu et al., Pharm. Res. 1996, 13:1856-1860, Klang et al., Int. J. Pharm. 1996, 132:33-44).

In all phospholipid-containing colloids (e.g. liposomes or emulsions), a significant decrease in zeta potential is observed overtime, due to the hydrolysis of phospholipids into free fatty acids (Zuidam and Crommelin, J Pharm Sci 1995, 84:1113-1119) which can be a source of toxic side effects following administration (Varveri et al., J. Photochem. Photobiol. A 1995, 91:121-124). In cationic phospholipids colloids, the decrease in zeta potential evidences that the system is not completely chemically stable (Tamilvanan et al., STP Pharma Sciences 2001, 11:421-426) and in some cases could result in the physical destabilization of the formulation as reflected by the droplet size.

For example, in chitosan cationic formulations containing 0.25-1.5% chitosan, 0-1.5% phospholipids, 0-2.5% poloxamer in a castor: soybean oil phase, only the formulation containing poloxamer with chitosan displayed good stability during autoclaving, while the coexistence of chitosan and phospholipids resulted in a destabilization of the emulsion during sterilization. According to the authors, the interaction between the positively charged chitosan with negatively-charged phospholipids which resulted in a damaged emulsifier film around the oil droplets provoked the coalescence of the droplets (Int. J Pharm. 1999, 183:175-84). These emulsions were evaluated further for their antimicrobial activity for mucosal or parenteral administration (Eur. J. Pharm. Biopharm. 2002, 53:115-23).

Of particular interest are the following patents dealing with cationic emulsions for topical ocular administration:

U.S. Pat. No. 6,007,826 discloses a cationic oil-in-water emulsion which comprises colloid particles with a positively charged interfacial film. The interfacial film is formed by cationic lipids (0.05-3% by weight) such as $C_{10}$-$C_{14}$ primary alkylamines (disclosed are stearylamine or oleylamine), $C_{10}$-$C_{24}$ primary alkanolamine or a cholesterol betainate; phospholipids (0.5-3%) and non-ionic surfactants from the group consisting of poloxamers, tyloxapol, polysorbate, and polyoxyethylene fatty acid esters (0.05-3%). The concentration of the oil is maintained within the 3-20% range. U.S. Pat. No. 6,007,826 emulsions zeta potential are not stable to thermal stress (see Tamilvanan et al., STP Pharma Sciences 2001, 11:421-426 and Example 12 as given here-after).

U.S. Pat. No. 6,656,460 to Benita and Lambert describes a method of treating a dry eye condition by topical application of a positive submicronic emulsion containing 0.1-0.5% phospholipids, 0.5-2% emulsifying agent such as poloxamer and benzalkonium chloride as a preservative. Since these preparations contain 0.1 to 0.5% by weight of phospholipids, their zeta potential is expected to decrease at 80° C. (see Example 12).

Although some of the prior art emulsions may show a good physical stability regarding droplet size, there is still a need for cationic ophthalmic emulsions which are physically stable, and which do not contain a sufficient amount of any substances susceptible of affecting the zeta potential overtime, while presenting a good tolerability for ocular administration.

Substances susceptible of affecting the zeta potential may be phospholipids, and any substances which become negatively charged upon storage.

The amount of substances affecting the zeta potential overtime must be such that at any time, the amount of positive charges in the emulsion is above the amount of negative charges.

By overtime in the meaning of this invention, it is meant a duration exceeding 1 year, preferably exceeding 2 years, more preferably exceeding 3 years. In this invention, if an emulsion meets any of tests A to D requirements, it is believed that said emulsion has a potential zeta that is not affected overtime.

By "good tolerability" in the present the invention, it is understood that the ratio therapeutic benefit to ocular discomfort is acceptable by the patient, and preferably similar to a placebo or NaCl 0.9% solution.

It is generally accepted that in order to show good ocular tolerability the cation content within the formulation should not exceed 0.1%, preferably not exceed 0.05% and even more preferably should not exceed 0.03%. Primary amines such as stearylamine or oleylamine were shown to be safe for ocular administration at 0.1% or 0.3% w/v (Klang et al., J. Pharm. Pharmacol. 1994, 46:986-993)

Quaternary amines such as benzalkonium chloride, benzododecinium bromide and benzethonium chloride are allowed by health authorities for ophthalmic administration up to concentration of approximately 0.03% (Furrer et al., Eur. J. Pharm. Biopharm. 2002, 53:263-280). Even though the presence of an important amount of cationic agent in emulsions may succeed in maintaining a stable positive zeta potential over time by cancelling emerging negative entities (see Example 13), such emulsions are not compatible with common recommendation for ophthalmic compositions. Attempts to reduce the cation concentration would lead to destabilization of the emulsions (see Example 14).

It is an object of this invention to propose submicron ophthalmic emulsions including minimal amounts of cationic agent and still having and keeping a stable positive zeta potential overtime.

The present invention relates to an ophthalmic oil-in-water type emulsion, which comprises colloid particles having an oily core surrounded by an interfacial film, said emulsion comprising at least one cationic agent and at least one non ionic surfactant, said emulsion having a positive zeta potential and meeting the zeta potential stability Test A, B, C and/or D requirements.

The emulsions according to the invention are physically stable overtime as defined hereabove and keep a positive zeta potential in the specific measurement conditions as described in Tests A, B, C and/or D.

According to the invention, the emulsions do not contain a sufficient amount of any substances susceptible of affecting the zeta potential overtime. Advantageously, the emulsions of the invention do not contain phospholipids.

Zeta Potential

Zeta potential measures a physical property which is exhibited by any particle in suspension. Zeta potential can be used to predict behaviour of the suspension in different environments, to optimize the formulations of suspensions and emulsions as well as to predict overtime stability.

In order to avoid the emulsion droplets to merge one with the other and form aggregates of successively increasing size, it is necessary to confer repulsive forces to the particles. One of the means to confer repulsive forces to a colloidal system is by electrostatic or charge stabilization. Electrostatic or charge stabilization has the benefits of stabilizing a system by simply altering the concentration of ions in the system. This is a reversible and inexpensive process.

There might by many origins of this surface charge depending upon the nature of the particle and its surrounding medium but the most important mechanisms are the ionisation of surface groups or the adsorption of charged ions.

The interaction of particles in polar liquids is not governed by the electrical potential at the surface of the particle, but by the effective potential of the particle and its associated ions. To utilize electrostatic control of dispersions, it is the zeta potential of the particle that must be measured rather than its surface charge. Charged particles will attract ions of opposite charge in the dispersant. Ions close to the surface are strongly bound; those further away form a more diffuse region. Within this region is a notional boundary, known as the slipping plane, within which the particle and ions act as a single entity. The potential at the slipping plane is known as the zeta potential. It has long been recognised that the zeta potential is a very good index of the magnitude of the interaction between colloidal particles and measurements of zeta potential are commonly used to assess the stability of colloidal systems. The zeta potential measured in a particular system is dependent on the chemistry of the surface, and also of the way it interacts with its surrounding environment. Therefore zeta potential must always be studied in a well defined environment (specifically pH and ionic strength).

Electrophoretic Mobility

An important consequence of the existence of electrical charges on the surface of particles is that they interact with an applied electric field. These effects are collectively defined as electrokinetic effects. If the motion is induced in a particle suspended in a liquid under the influence of an applied electric field, it is more specifically named electrophoresis. When an electric field is applied across an electrolyte, charged particles suspended in the electrolyte are attracted towards the electrode of opposite charge. Viscous forces acting on the particles tend to oppose this movement. When equilibrium is reached between these two opposing forces, the particles move with constant velocity. The velocity is dependent on the strength of electric field or voltage gradient, the dielectric constant of the medium, the viscosity of the medium and the zeta potential. The velocity of a particle in a unit electric field is referred to as its electrophoretic mobility. Zeta potential is related to the electrophoretic mobility by the Henry equation:

$$U_E = 2 \frac{\varepsilon}{3\eta} z \, f(\kappa a)$$

where $U_E$=electrophoretic mobility, z=zeta potential, $\varepsilon$=dielectric constant, $\eta$=viscosity and $f(Ka)$=Henry's function.

Electrophoretic determinations of zeta potential are most commonly made in aqueous media and moderate electrolyte concentration. f(xa) in this case is 1.5, and this is referred to as the Smoluchowski approximation. Therefore calculation of zeta potential from the mobility is straightforward for systems that fit the Smoluchowski model, i.e. particles larger than about 0.2 microns dispersed in electrolytes containing more that 10-3 molar salt. For small particles in low dielectric constant media (eg non-aqueous media), f(Ka) becomes 1.0 and allows an equally simple calculation. This is referred to as the Huckel approximation.

Tests A, B, C and D

Test A consists in measuring the stability of the emulsion zeta potential under thermal stress conditions.

Zeta potential of the emulsion is measured at T=0, i.e. as soon as the emulsion has been prepared, the obtained value being named $Z_0$. Glass vials (Type I) of 10 ml effective capacity containing between 5-10 ml of emulsion and sealed under nitrogen atmosphere (without bubbling) are stored at 80° C.

Then at T=15 hours the zeta potential $Z_{15h}$ is measured.

The value $\delta A = Z_{15h} - Z_0$ is then calculated.

For each measurement of the zeta potential, it is operated as follows:

The zeta potential of the emulsion droplet surface is determined by electrophoretic mobility in an apparatus such as a Malvern Zetasizer 2000 (Malvern Instruments, UK) equipped with suitable software and calibrated with the supplied standard.

The emulsion is diluted in double distilled water if needed in order to obtain the scattering intensity allowing optimal particle detection. The sample count rate should be between 100 to 1000 KCps, in homodyne detection (if heterodyne detection is used, the contribution of the reference beam should be deduced). Three consecutive measurements are performed at 25° C. using a constant cell drive of 150 mV. The electrophoretic mobility is converted into zeta potential values through the Smoluchowsky equation, using the dielectric constants and viscosity of water. The measured value corresponds to the average of the 3 obtained values.

It is considered that the emulsion meets zeta potential stability Test A if $\delta A$ is less than the standard error of measurements, preferably less than 10 mV, and even more preferably less than 5 mV.

According to an advantageous embodiment, the ophthalmic emulsion according to the invention meets zeta potential stability Test B.

Test B is similar to Test A except that the emulsion is stored during 48 hours at 80° C., the zeta potential $Z_2$ is measured on after 48 hours and $\delta B = Z_2 - Z_0$ is calculated. The emulsion is considered as meeting the requirements of zeta potential stability test B if $\delta B$ is less than the standard error of measurements, preferably less than 10 mV, and even more preferably less than 5 mV.

According to a more advantageous embodiment of the invention, the ophthalmic emulsion according to the invention meets zeta potential stability Test C.

Test C is similar to Test A except that the emulsion is stored during 7 days at 80° C., the zeta potential $Z_7$ is measured on day 7 and $\delta C = Z_7 - Z_0$ is calculated. The emulsion is considered as meeting the requirements of zeta potential stability test C if $\delta C$ is less than the standard error of measurements, preferably less than 10 mV, and even more preferably less than 5 mV.

According to a still more advantageous embodiment of the invention, the ophthalmic emulsion according to the invention meets zeta potential stability Test D.

Test D is similar to Test A except that the emulsion is stored during 14 days at 80° C., the zeta potential $Z_{14}$ is measured on day 14 and $\delta D = Z_{14} - Z_0$ is calculated. The emulsion is considered as meeting the requirements of zeta potential stability test D if $\delta D$ is less than the standard error of measurements, preferably less than 10 mV, and even more preferably less than 5 mV.

According to an embodiment of the invention, the concentration of the cationic agent is comprised between 0.001 and 0.1%, preferably between 0.002 and 0.05%, and still more preferably between 0.003 and 0.03% by weight of the total weight of the emulsion (w/w).

Advantageously, the concentration of the oil is not higher than 7%, preferably about 0.5 to 5%, and still more preferably about 1 to 3% by weight of the total weight of the emulsion (w/w).

In another embodiment of the invention, the weight ratio cationic agent/oil is comprised between 0.0025 and 0.06, preferably between 0.005 and 0.04, preferably from 0.01 to 0.02.

In the emulsion according to the invention, the concentration of non-ionic agent is less than 1%, preferably comprised between 0.01 to 0.6% by weight of the total weight of the emulsion (w/w).

In the ophthalmic oil-in-water emulsion according to the invention, the cationic agent is selected in the group consisting of $C_{10}$-$C_{24}$ primary alkylamines, tertiary aliphatic amines, quaternary ammonium compounds, cationic lipids, amino alcohols, biguanide salts, cationic polymers and the mixture of two or more thereof.

The primary amine is preferably selected from the group consisting of oleylamine and stearylamine; the tertiary aliphatic salt can be dimethyl lauramine or diethanolamine, the amino alcohol can be tris(hydroxymethyl)aminomethane.

In a preferred embodiment, the cationic agent is a quaternary ammonium compound preferably selected from the group consisting of benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristalkonium halide, stearalkonium halide or a mixture of two or more thereof, halide being preferably chloride or bromide. Advantageously, said cationic agent can be selected from the group comprising benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof.

The cationic polymer can be chitosan, the cationic lipid can be 1,2-dioleyl-3-trimethylammonium-propane, 1,2-dioleoyl-sn-glycero-phosphatidylethanolamine, cationic glycosphingo-lipids or cationic cholesterol derivatives.

Examples of biguanide salts may be selected from the group comprising chlorhexidine and salts thereof, polyaminopropyl biguanide, phenformin, alkylbiguanide or a mixture of two or more thereof.

Examples of non-ionic surfactants which may be included in the emulsion of the invention are tyloxapol, poloxamers such as Pluronic F68LF™ or Lutrol F68, Pluronic L-$G_2$LF™ and Pluronic L62D™ (BASF Wyandotte Corp., Parsippany, N.J., USA), polysorbates such as polysorbate 20 and polysorbate 80, polyoxyethylene castor oil derivatives, sorbitan esters, polyoxyl stearates and a mixture of two or more thereof.

Advantageously, the oil-in-water emulsion according to the instant invention comprises benzalkonium chloride as cationic agent and tyloxapol as one of the non-ionic surfactants.

According to another advantageous mode, the emulsion comprises benzalkonium chloride as cationic agent and tyloxapol and poloxamer as non-ionic surfactants.

According to the invention, the colloidal particles have an average particle size of equal or less than 1 μm, advantageously equal or less than 300 nm, more advantageously in the range of 100 to 250 nm.

The oil phase of the emulsion may comprise one or more components selected from the group consisting of vegetable oils (i.e. soybean oil, olive oil, sesame oil, cotton seed oil, castor oil, sweet almond oil), mineral oil (i.e. petrolatum and liquid paraffin), medium chain triglycerides (MCT) (i.e. a triglyceride oil in which the carbohydrate chain has about 8-12 carbon atoms), oily fatty acid, isopropyl myristate, oily fatty alcohols, esters of sorbitol and fatty acids, oily sucrose esters, and in general any oily substance which is physiologically tolerated.

The major component of the oily phase will preferably be either vegetable oil and/or MCT. Fatty acids or fatty alcohols may be included in cases where the hydrophobic substance to be carried by the emulsion is not sufficiently soluble in the oily phase.

Examples of MCT oil which may be used in emulsions of the present invention are TCM™ (Societe des Oleagineux, France), Miglyol 812™ (Dynamit Novel, Sweden).

Other optional compounds which may be present in the emulsion according to the invention are for example anionic surfactants and various additives such as osmotic pressure regulators, e.g. sucrose, glycerine or mannitol; antioxidants, e.g. alpha-tocopherol, sodium bisulfite, sodium metasulfite, sodium thiosulfate anhydrous, citric acid monohydrate, ascorbyl palmitate and ascorbic acid; or preservatives, e.g. thiomersal, chlorobutanol, benzyl alcohol, phenoxyethanol, phenylethyl alcohol, sorbic acid, EDTA and methyl-, ethyl-, or butyl paraben; said optional compounds may only be added in specific concentrations that do not impair the zeta potential stability.

Examples of anionic surfactants are anionic lipids intended for pharmaceutical such as phospholipids. Examples of phospholipids, which may be used in the emulsions of the invention, are lecithins; Epikuren 120™ (Lucas Meyer, Germany) which is a mixture of about 70% phosphatidylcholine and 12% phosphatidylethanclamine and about 15% other phospholipids; Ovothin 160™ or Ovethin 200™ (Lucas Meyer, phosphatidylcholine, 18% phosphatidylethanolamine and 12% other phospholipids; a purified phospholipids mixture, e.g. such which is obtained from egg yolk; Lipoid $E_{80}$™ (Lipoid AC, Ludwigshaf en, Germany) which is a phospholipid mixture comprising about 80% phosphatidylcholine, 8% phosphatidylethanolamine, 3.6% non-polar lipids and about 2% sphingomyeline.

A preferred pH in the aqueous phase of the emulsion of the invention is 4.0-8.5, 6.0-8.0 being particularly preferred.

This invention also relates to a process for the preparation of an ophthalmic oil-in-water type emulsion according to the invention, which comprises colloid particles having an oily core surrounded by an interfacial film, said emulsion comprising at least one cationic agent, at least one non ionic surfactant said emulsion having a positive zeta potential and meeting zeta potential stability Test A requirements, said process comprising the steps of shear mixing and then high pressure homogenization of the coarse emulsions obtained through mixing of the aqueous and the oily phases.

Ophthalmic emulsions in accordance with the present invention may be formulated into pharmaceutical compositions with various hydrophobic active ingredients for a large number of pharmaceutical applications. Also hydrophilic agents can be administered with these emulsions.

According to the invention, the emulsion may be formulated for ocular administration of said active ingredients. In this oil-in-water emulsion, the water-insoluble drug is solubilized in the internal oil phase, thereby remaining in the preferred molecular state. In addition, the blurred vision caused by oils is minimised by the water in the external phase. Furthermore, the concentration of the drug in the oil phase can be adjusted to maximise thermodynamic activity, thus enhancing drug penetration to deeper tissues.

Consequently, the instant invention provides the use of an oil-in-water emulsion according to the instant invention for the preparation of a medicament useful for preventing or treating ophthalmic disorders.

The invention also concerns ophthalmic formulations comprising an oil-in-water emulsion according to the instant invention and a pharmaceutically acceptable carrier selected from the group comprising eye drop composition, eye ointment, ophthalmic gel.

Said formulations may also comprise a pharmaceutically effective amount of an active ingredient in or within the pharmaceutically acceptable carrier.

The instant invention also provides a method of treatment of ocular conditions comprising a pharmaceutical composition comprising an oil-in-water type emulsion as defined above.

The invention also relates to the use of an oil-in-water emulsion according to the instant invention or of an ophthalmic composition as defined above for the preparation of a medicament for the treatment of ocular conditions.

A wide variety of ocular conditions such as glaucoma, ocular inflammatory conditions such as keratitis, uveitis, intra-ocular inflammation, allergy and dry-eye syndrome ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), retinal diseases associated with glial proliferation may be prevented or treated using the cationic emulsions according to the present invention.

Some substances suitable for delivery to the eye may include, for example, antibiotics (such as tetracycline, chlortetracycline, bacitracin, neomycin, polymyxin, gramicidin, cephalexin, oxytetracycline, chloramphenicol, kanamycin, rifampicin, tobramycin, gentamycin, ciprofloxacin, aminosides, erythromycin and penicillin, quinolone, ceftazidime, vancomycine imipeneme); antifungals such as amphotericin B and miconazole; antibacterials such as sulfonamides, sulfadiazine, sulfacetamide, sulfamethizole and sulfisoxazole, nitrofurazone and sodium propionate; antivirals, such as idoxuridine, trifluorotymidine, acyclovir, ganciclovir, cidofovir and interferon; antibacterial agents such as nitrofurazone and sodium propionate; non-antibiotic, anti-infection, anti-bacterial or anti-microbial drugs such as iodine based preparation triclosan, chlorhexidine; antiallergenics such as sodium cromoglycate, antazoline, methapyriline, chlorpheniramine, cetirizine, pyrilamine and prophenpyridamine; antiproliferative agents such as thalidomide; synthetic gluocorticoids and mineralocerticoids and more generally hormones forms derivating from the cholesterol metabolism (progesterone, estrogens, androgenic hormones such as testosterone, DHEA and their derivatives); anti-inflammatories such as hydrocortisone, hydrocortisone acetate, dexamethasone, dexamethasone 21-phosphate, fluorocinolene, medrysone, prednisolone acetate, luoromethalone, triamcinolone and triamcinolene acetonide and their derivatives;

non-steroidal anti-inflammatories such as salicylate, indomethacin, ibuprofen, diclofenac, flurbiprofen and piroxicam and COX2 inhibitors such as rofecoxib, diclofenac, nimesulide, nepafenac; antineoplastics such as carmustine, cisplatin, mitomycin and fluorouracil; immunological drugs such as vaccines and immune stimulants; insulin, calcitonin, parathyroid hormone and peptide and vasepressin hypothalamus releasing factor; beta adrenergic blockers such as timolol maleate, levobunolol HCl and betaxolol HCl, timolol-base, betaxolol, atenolol, epinephrine, dipivalyl, oxonolol, acetazolamide-base and methazolamide; cytokines, interleukins, and growth factors (growth factors such as epidermal growth factor, fibroblast growth factor, platelet derived growth factor, transforming growth factor beta, ciliary neurotrophic growth factor, glial derived neurotrophic factor, NGF, EPO, P1GF); antibodies or antibodies fragments, oligoaptamers, aptamers and gene fragments (oligonucleotides, plasmids, ribozymes, small interference RNA, nucleic acid fragments, peptides, antisense sequences); immunosuppressants such as cyclosporine, sirolimus and tacrolimus, immunomodulators such as endoxan, tamoxifene; antithrombolytic and vasodilator agents such as rtPA, urokinase, plasmin, nitric exide denors; antioxidants such as lutein, vitamins and/or their derivatives; and/or optically acceptable salts thereof.

According to an advantageous embodiment, the active substance is at least one immunosuppressive agent, preferably chosen in the group consisting of cyclosporine, preferably cyclosporin A, tacrolimus and sirolimus. Advantageously, in these emulsions the immunosuppressive agents is in an amount of 0.01 to 0.4%, preferably 0.05 to 0.2% (w/w). Advantageously, these emulsions do not contain phospholipids. Advantageously, these emulsions of the invention contain cyclosporine, sirolimus and/or tacrolimus in a vehicle comprising or consisting of MCT. Without being linked by a theory, the use of MCT, a vegetal oil selected among all, may provide stability and bioavailability to the ophthalmic emulsions of the invention containing at least one immunosuppressive agent, preferably cyclosporine A. MCT has been found to have good solubilizing properties of cyclosporine, which may play a role in the observed improved bioavailability of cyclosporine in the emulsions of the invention. Advantageously, the amount of MCT is from 0.5 to 4% w/w of the emulsion. Advantageously, the emulsion of the invention contains an immunosuppressive agent, preferably chosen in the group consisting of cyclosporine, preferably cyclosporin A, tacrolimus and sirolimus, and MCT and tyloxapol. Advantageously, the amount of tyloxapol is from 0.05 to 0.5% w/w of the emulsion. Preferably, the weight ratio of immunosuppressive agent to oil is from 0.0125 to 0.1. In a particular embodiment of the emulsion the weight ratio of immunosuppressive agent to oil is from 0.083 to 0.1. In another particular embodiment of the emulsion, the weight ratio of immunosuppressive agent to oil is from 0.0125 to 0.05. The emulsions of the invention containing at least one immunosuppressive agent are particularly useful to treat dry eye conditions, in particular keratoconjunctivitis sicca (KCS), atopic keratoconunctivitis sicca (AKC) and vernal keratoconjunctivitis (VKC).

The invention also relates to the use of an oil-in-water emulsion containing or not an active substance for the preparation of an ophthalmic composition for treating dry-eye conditions.

The emulsion according to the invention may also be included in a delivery device selected from the group comprising lenses, ocular patch, implant or insert.

The drug or active substance may be present in an amount of about 0.0001 to 5% by weight of the emulsion. Depending upon whether the drug is hydrophilic or hydrophobic, it will be physically present in the oily phase or in the aqueous component.

The best mode of making and using the present invention are described in the following examples. These examples are given only to provide direction and guidance in how to make and use the invention, and are not intended to limit the scope of the invention in any way.

EXAMPLES

In the following examples, the following abbreviations are used:

CTAB: mixture of hexadecytrimethyl ammonium bromide, tetradecyltrimethylammonium bromide and dodecyltrimethylammonium bromide
MCT: TCM™ (Société des Oléagineux, France)
BAK: benzalkonium chloride
BEC: benzethonium chloride
BCB: benzyldimethyldodecylammonium bromide
OA: Oleylamine (Sigma (USA)
SA: Stearylamine (Sigma, USA)
CsA: Cyclosporin A
Cremophor: Cremophor EL (BASF, France)
Lutrol: Lutrol F68 (BASF, France)
Oxypol (Gattefosse, France)
Montane 20 (SEPPIC, France)
Oxypol: Gattefosse (St Priest, France)
Montane 20 (SEPPIC, France)
Lipoid E80 (LIPOID GmbH, Germany)

Example 1

Preparation of Cationic Emulsions Wherein the Cationic Agent is CTAB

Methods:

| Component | Z01EM042 | Z01EM043 |
|---|---|---|
| CTAB (cationic agent) | 0.05% | 0.1% |
| MCT (oil) | 2% | 2% |
| Alpha-tocopherol (antioxidant) | 0.01% | 0.01% |
| Lipoid E80 ™ (anionic surfactant) | 0.32% | 0.32% |
| Lutrol F68 ™ (non ionic surfactant) | 0.5% | 0.5% |
| Glycerin (tonicity agent) | 2.25% | 2.25% |
| Water | 94.87% | 94.82% |

The oily phase components were successively weighed in the same beaker and then magnetically stirred under a slight heating (40° C.) until a yellow, limpid and slightly viscous phase is obtained. Aqueous phase components were successively weighed in the same beaker and then magnetically stirred under a slight heating (40° C.) until a transparent, limpid and fluid phase is obtained. Both phases were heated to 65° C. The coarse emulsion was formed by rapid addition of the aqueous phase in the oily phase and was then rapidly heated to 75° C. The aqueous phase and coarse emulsion beakers were protected by a film to avoid any water evaporation. The emulsion was white and slightly transparent. The emulsion droplet size was then decreased by a 5 minutes high shear mixing with a POLYTRON PT 6100. The emulsion became milky. The emulsion temperature was cooled down to 20° C. using an ice bath.

The final emulsion was obtained by homogenization in a microfluidizer (C5, Avestin) using continuous cycles for 5 min at a pressure of 10,000 psi. The emulsion was milky, very fluid and did not adhere on the glass. The emulsion temperature was decreased to 25° C. Its pH was measured and then adjusted to 8.00 using a 0.1 M HCl or 0.1 M NaOH solution. Emulsion was conditioned in tinted glass vials with nitrogen bubbling and then sterilized in an autoclave 20 minutes at 121° C.

The mean particle size of the emulsions droplets was determined by quasi-elastic light scattering after dilution in water using a High Performance Particle Sizer (Malvern Instruments, UK). The electrophoretic mobility was measured at 25° C. in a Malvern Zetasizer 2000 (Malvern Instruments, UK) following a 1:200 dilution in double distilled water as detailed above.

Results:

|  | Z01EM042 | Z01EM043 |
| --- | --- | --- |
| Droplet size (nm) | 126 | 128 |
| Zeta potential (mV) | 36.4 | 49.5 |

Example 2

Stability of Cationic Emulsions Described in Example 1

Methods:

The stability of the autoclaved emulsions (droplet size, zeta potential) at 80° C. was monitored for 14 days.

Results:

|  | Z01EM042 | | | Z01EM043 | | |
| --- | --- | --- | --- | --- | --- | --- |
| T(days) | 0 | 7 | 14 | 0 | 7 | 14 |
| Droplet size (nm) | 126 | 143 | 155 | 128 | 140 | 151 |
| Zeta potential (mV) | 36.4 | 39.0 | 38.7 | 49.5 | 53.8 | 49.9 |

Z01EM042 and Z01EM043 meet zeta potential stability test D requirements.

Example 3

Preparation of a Cationic Emulsion Wherein the Cationic Agent is Benzalkonium Chloride Methods:

| Component | Z01EM042 |
| --- | --- |
| BAK (cationic agent) | 0.02% |
| MCT (oil) | 1% |
| Alpha-tocopherol (antioxidant) | 0.005% |
| Tyloxapol (non ionic surfactant) | 0.16% |
| Lutrol F68 (non ionic surfactant) | 0.5% |
| Glycerin (tonicity agent) | 2.25% |
| Water | 96.07% |

Preparation according to the process described in Example 1.

Results:

|  | Z01EM093 |
| --- | --- |
| Zeta potential (mV) | 20.4 |

Example 4

Stability of a Cationic Emulsion Described in Example 3

Methods:

The stability of the autoclaved emulsion (zeta potential) at 80° C. was monitored for 15 days.

Results:

|  | Z01EM093 | | | | | | |
| --- | --- | --- | --- | --- | --- | --- | --- |
| T(days) | 0 | 2 | 5 | 7 | 9 | 12 | 14 |
| Zeta potential (mV) | 20.4 | 23.2 | 21.5 | 21.6 | 22.7 | 21.0 | 21.3 |

The zeta potential of the emulsion presented in this example was more stable than previously known formulations (data not shown). Z01EM093 meets zeta potential stability test D requirements.

Example 5

Cationic Emulsions Wherein the Cationic Agent is Oleylamine

Methods:

| % w/w | Z01EM165 |
| --- | --- |
| Oleylamine | 0.05 |
| Mineral oil | 1 |
| LutrolF68 | 0.1 |
| Tyloxapol | 0.3 |
| glycerin | 2.25 |
| Water | Up to 100 |

Preparation according to the process described in Example 1.

Results:

|  | Z01EM165 | |
| --- | --- | --- |
| T(days) | Droplet size(nm) | Zeta potential(mV) |
| 0 | 186 | 51.3 |
| 3 | 184 | 47.2 |
| 8 | 194 | 52.1 |
| 13 | 163 | 48.2 |
| 15 | 175 | 47.9 |

Z01EM165 meets zeta potential stability test D requirements.

Example 6

Methods:

| % (w/w) | Z01EM092 |
|---|---|
| CTAB | 0.005 |
| MCT | 1 |
| Vitamin E | 0.005 |
| Tyloxapol | 0.16 |
| Lutrol | 0.25 |
| Glycerin | 2.25 |
| Water | Up to 100 |

Preparation according to the process described in Example 1.

Results:

| Emulsion | Z01EM092 | | | | | | |
|---|---|---|---|---|---|---|---|
| T(days) | 0 | 2 | 5 | 7 | 9 | 12 | 14 |
| Zeta potential (mV) | 19.8 | 21.9 | 22.4 | 18.5 | 20.3 | 18.5 | 20.5 |

Z01EM092 meets zeta potential stability test D requirements.

Example 7

Cationic Emulsions with BAK

Methods:

| | Emulsion | | | |
|---|---|---|---|---|
| Components | Z01EM105 | Z01EM155 | Z01EM162 | Z01EM163 |
| | % (w/w) | | | |
| BAK | 0.02 | 0.02 | 0.02 | 0.02 |
| MCT | 2 | 1 | 1 | 1 |
| Castor oil | 0 | 1 | 0 | 0 |
| Cremophor | 0 | 0.25 | 0.1 | 0 |
| Tyloxapol | 0.32 | 0 | 0.3 | 0.3 |
| Montane 20 | 0 | 0 | 0 | 0.1 |
| Lutrol | 0.5 | 0.1 | 0 | 0 |
| Oxypol | 0 | 0.25 | 0 | 0 |
| Vitamin E | 0.01 | 0 | 0 | 0 |
| Glycerin | 2.25 | 2.25 | 2.25 | 2.25 |
| water | Up to 100% | Up to 100% | Up to 100% | Up to 100% |

The stability of the autoclaved emulsions (droplet size, zeta potential) at 80° C. was monitored T=0, 7 and 14 days.

Results:

| | T(days) | Z01EM105 | Z01EM155 | Z01EM162 | Z01EM163 |
|---|---|---|---|---|---|
| Droplet size (nm) | 0 | nd | 288 | 243 | 249 |
| | 7 | nd | 290 | 261 | 262 |
| | 14 | nd | nd | 264 | 234 |
| Zeta potential (mV) | 0 | 24.9 | 19.7 | 22.3 | 18.8 |
| | 2 | 20.7 | nd | nd | Nd |
| | 7 | 21.3 | 14.2 | 14.7 | 16.5 |
| | 10 | 23.2 | nd | nd | Nd |
| | 13 | 22.2 | nd | nd | Nd |
| | 14 | nd | nd | 17.4 | 15.7 |
| | 15 | 23.2 | nd | nd | Nd | nd: not determined

Z01EM105, Z01EM162 and Z01EM163 meet zeta potential stability test D requirements. Z01EM115 meets zeta potential stability test C requirements.

Example 8

Cationic Emulsions Wherein the Cationic Agent is BEC or BCB

Methods:

| | Emulsion | |
|---|---|---|
| components | Z01EM170 | Z01EM171 |
| | % (w/w) | |
| BEC | 0.02 | 0 |
| BCB | 0 | 0.02 |
| MCT | 2 | 2 |
| Tyloxapol | 0.3 | 0.3 |
| Glycerin | 2.25 | 2.25 |
| Lutrol | 0.1 | 0.1 |
| water | Up to 100% | Up to 100% |

Preparation According to the Process Described in Example 1.

Results:

| | T(days) | Z01EM170 | Z01EM171 |
|---|---|---|---|
| Droplet size (nm) | 0 | 210 | 239 |
| | 7 | 232 | 250 |
| | 14 | 233 | nd |
| Zeta potential (mV) | 0 | 23.2 | 9.1 |
| | 7 | 22.4 | 6.4 |
| | 14 | 24.1 | 7.2 |

Z01EM170 and Z01EM171 meet zeta potential stability test D requirements.

Example 9

Cationic Emulsion with BAK and Mineral Oil

Methods:

| Emulsion Components | Z01EM151 | Z01EM152 | Z01EM153 % (w/w) | Z01EM164 | Z01EM173 |
|---|---|---|---|---|---|
| BAK | 0.02 | 0.02 | 0.02 | 0.02 | 0.02 |
| Mineral oil | 1 | 1 | 1 | 1 | 1 |
| Tyloxapol | 0.3 | 0.3 | 0.3 | 0.3 | 0.3 |
| Lutrol | 0.1 | 0.1 | 0.1 | 0.1 | 0.1 |
| Glycerin | 2.25 | 2.25 | 2.25 | 2.25 | 2.25 |
| Water | Up to 100% | Up to 100% | Up to 100% | 0 | 0 |
| Buffer | 0 | 0 | 0 | Up to 100% | Up to 100% |

The stability of the autoclaved emulsions (droplet size, zeta potential) at 80° C. was monitored for 14 days.

Results:

| | T(days) | Z01EM151 | Z01EM152 | Z01EM153 | Z01EM164 | Z01EM173 |
|---|---|---|---|---|---|---|
| Droplet size (nm) | 0 | 25.8 | 26.0 | 23.4 | 16.7 | 20.7 |
| | 3 | 22.2 | 23.0 | 26.2 | 18.3 | nd |
| | 5 | 23.5 | 23.3 | 24.2 | nd | nd |
| | 7 | nd | nd | nd | nd | 19.7 |
| | 8 | nd | nd | nd | 16.5 | nd |
| | 10 | 34.1 | 20.4 | 17.7 | nd | nd |
| | 12 | 23.3 | 21.7 | 23.9 | nd | nd |
| | 13 | nd | nd | nd | 12.7 | nd |
| | 14 | 23.9 | 23 | 20.3 | nd | nd |
| | 15 | nd | nd | nd | 13.2 | 17.8 |
| Zeta potential (mV) | 0 | 174 | 220 | 185 | 209 | 200 |
| | 3 | 178 | 215 | 184 | 200 | nd |
| | 5 | 170 | 213 | 182 | nd | nd |
| | 7 | nd | nd | nd | 213 | 200 |
| | 8 | nd | nd | nd | nd | nd |
| | 10 | 182 | 311 | 186 | nd | nd |
| | 12 | 176 | 221 | 224 | nd | nd |
| | 13 | nd | nd | nd | 218 | nd |
| | 14 | 168 | 216 | 188 | nd | nd |
| | 15 | nd | nd | nd | 203 | 216 |

All emulsions meet zeta potential stability test D requirements.

Example 10

Cationic Emulsions Containing Cyclosporin A (CsA) as Active Substance in the Oil Phase Methods and Results:

Preparation according to the process described in Example 1, with the cyclosporin added to the oil phase.

The stability of the autoclaved emulsions (droplet size, zeta potential) at 80° C. was monitored T=0, 7 and 15 days.

| Emulsion | Z06EM044 | Z06EM045 | | |
|---|---|---|---|---|
| Composition | 0.02% BAK<br>1.5% MCT<br>0.24% Tyloxapol<br>0.01% vit E<br>0.375% Lutrol<br>2.25% Glycerin<br>Water to 100%<br>CsA 0.1% | 0.02% BAK<br>2% MCT<br>0.32% Tyloxapol<br>0.01% vit E<br>0.5% Lutrol<br>2.25% Glycerin<br>Water to 100%<br>CsA 0.2% | | |
| Zeta potential (mV) | T0: 224<br>T7: 220<br>T15 239 | T0: 216<br>T7: 214<br>T15: 211 | | |
| Droplet size (nm) | T0: 25.3<br>T7: 22.9<br>T15: 21.8 | T0: 24.8<br>T7: 22.2<br>T15: 20.8 | | |
| Emulsion | Z06EM046 | Z06EM047 | Z06EM048 | Z06EM049 |
| Composition | 0.02% BAK<br>1% MCT<br>0.16% Tyloxapol<br>0.01% vit E<br>2.25% Glycerin<br>Water to 100%<br>CsA 0.05% | 0.02% BAK<br>0.75% MCT<br>0.12% Tyloxapol<br>0.01% vit E<br>0.1% Lutrol<br>2.25% Glycerin<br>Water to 100%<br>CsA 0.025% | 0.02% BAK<br>2% MCT<br>0.3% Tyloxapol<br>0.01% vit E<br>0.1% Lutrol<br>2.25% Glycerin<br>Water to 100%<br>CsA 0.025% | 0.02% BAK<br>1% MCT<br>0.16% Tyloxapol<br>0.01% vit E<br>0.1% Lutrol<br>2.25% Glycerin<br>Water to 100%<br>CsA 0.05% |
| Zeta potential (mV) | T0: 22.7<br>T7: 20.7<br>T15: 20.7 | T0: 20.9<br>T7: 18.9<br>T15: 16.9 | T0: 19.6<br>T7: 19.6<br>T15: 19.4 | T0: 25.0<br>T7: 24.7<br>T15: 19.2 |
| Droplet size (nm) | T0: 188<br>T7: 186<br>T15: 195 | T0: 165<br>T7: 188<br>T15: 194 | T0: 212<br>T7: 193<br>T15: 200 | T0: 159<br>T7: 173<br>T15: 177 |
| Emulsion | Z06EM050 | Z06EM051 | Z06EM052 | Z06EM053 |
| Composition | 0.02% BAK<br>2% MCT<br>0.3% Tyloxapol<br>0.01% vit E<br>0.1% Lutrol<br>2.25% Glycerin<br>Water to 100%<br>CsA 0.05% | 0.02% BAK<br>2% MCT<br>0.3% Tyloxapol<br>0.01% vit E<br>0.1% Lutrol<br>2.25% Glycerin<br>Water to 100%<br>CsA 0.2% | 0.02% BAK<br>4% MCT<br>0.3% Tyloxapol<br>0.01% vit E<br>0.1% Lutrol<br>2.25% Glycerin<br>Water to 100%<br>CsA 0.2% | 0.02% BAK<br>2% MCT<br>0.3% Tyloxapol<br>0.01% vit E<br>0.1% Lutrol<br>2.25% Glycerin<br>Water to 100%<br>CsA 0.1% |
| Zeta potential (mV) | 0: 17.9<br>T7: 20.3<br>T15: 18.9 | T0: 20.1<br>T7: 21.9<br>T15: 19.0 | T0: 28.4<br>T7: 24.5<br>T15: 23.0 | T0: 23.5<br>T7: 23.2<br>T15: 20.3 |
| Droplet size (nm) | T0: 224<br>T7: 212<br>T15: 221 | T0: 179<br>T7: 195<br>T15: 206 | T0: 176<br>T7: 201<br>T15: 195 | T0: 204<br>T7: 211<br>T15: 226 |

Emulsions containing CsA as active substance satisfy zeta potential stability test D requirements.

Example 11

Cationic Emulsions whose Zeta Potential is not Stable Over Time

Methods and Results:
Preparation according to the process described in Example 1.

| | Emulsion | |
|---|---|---|
| | Z01EM102 | Z01EM172 |
| Composition | 0.05% SA<br>1 MCT<br>0.16% Lipoid<br>0.005% Vit E<br>0.25% Lutrol<br>2.25% Glycerin<br>Water to 100% | 0.12% SA<br>0.01% BAK<br>2.5% MCT<br>0.5% Lipoid<br>0.01% Vit E<br>0.42% Lutrol<br>2.25% Glycerin<br>Water to 100% |
| Zeta potential (mV) | T0: 60.6<br>T2: 39.1<br>T7: 10.0 | T0: 55.8<br>T7: 27.8<br>T15: 4.3 |
| Droplet size (nm) | T0: 161<br>T2: 158<br>T7: ND | T0: 166<br>T7: 164<br>T15: 176 |

The stability of the autoclaved emulsions (droplet size, zeta potential) at 80° C. was monitored at T=0, 7 and 15 days.

Z01EM102 and Z01EM172 do not meet zeta potential stability test C requirements.

Example 12

Cationic Emulsion Containing Very High Cation Content Whose Zeta Potential is Stable Over Time, and which is not Suitable for Ophthalmic Use Methods and Results:
Preparation according to the process described in Example 1.

| Emulsion | Z01EM186 |
|---|---|
| Composition | 1% BAK |
| | 10% Soybean oil |
| | 1.2% Lipoid |
| | 2.25% Glycerin |
| | Water to 100% |
| Zeta potential (mV) | T0: 57.5 |
| | T7: 55.1 |
| | T15: 53.9 |
| Droplet size (nm) | T0: 182 |
| | T7: 198 |
| | T15: 212 |

The stability of the autoclaved emulsion (droplet size, zeta potential) at 80° C. was monitored at T=0, 7 and 15 days.

Although Z01EM186 meet zeta potential stability test D requirements, its cationic agent concentration (BAK) is 50-fold that generally used for topical ocular administration. Said emulsion is not suitable as ophthalmic emulsion.

Example 13

Cationic Emulsion Containing Lutein as Active Ingredient

Method: As described previously.

| | Z42EM001 | Z42EM002 |
|---|---|---|
| Lutein | 0.4 | 0.4 |
| Safflower oil | 1.6 | 1.6 |
| Tyloxapol | 0.3 | 0.3 |
| Montane 20 | — | 0.1 |
| BAK | 0.02 | 0.02 |
| Poloxamer | 0.1 | 0.1 |
| Glycerol | 2.25 | 2.25 |
| Deionised water | qsp 100 | qsp 100 |

Preparation according to the process described in Example 1.

| | | Z42EM001 | Z42EM002 |
|---|---|---|---|
| Droplet size (nm) | T0 | 347 | 255 |
| | T7 | 290 | 236 |
| | T14 | 285 | 321 |
| Zeta potential (mV) | T0 | 15.8 | 16.0 |
| | T7 | 8.8 | 8.4 |
| | T14 | 7.1 | 8.9 |

Emulsions containing lutein as active substance satisfy zeta potential stability test D requirements

Example 14

Cationic Emulsion Containing Low Cation Content Whose Zeta Potential and/or Droplet Size are not Stable Over Time Methods and Results:
Preparation according to the process described in Example 1.
The stability of the autoclaved emulsion (droplet size, zeta potential) at 80° C. was monitored at T=0, 7 and 15 days.

| | Emulsion | |
|---|---|---|
| | Z01EM086 | Z01EM089 |
| Composition | 0.01% CTAB | 0.02% BAK |
| | 2% MCT | 2% MCT |
| | 0.32% Lipoid | 0.32% Lipoid |
| | 0.01% Vit E | 0.01% Vit E |
| | 0.5% Lutrol | 0.5% Lutrol |
| | 2.25% Glycerin | 2.25% Glycerin |
| | Water to 100% | Water to 100% |
| Zeta potential (mV) | T0: 41.6 | T0: 33.7 |
| | T7: 29.8 | T7: 20.4 |
| | T15: −15.6 | T15: −5.1 |
| Droplet size (nm) | T0: 155 | T0: 141 |
| | T15: 167 | T15: 172 |

Z01EM086 and Z01EM089 do not meet zeta potential stability test C requirements.

Example 14

Ocular Tolerability Test After Chronic Topical Administration

The aim of this study was to determine the ocular tolerance of cationic emulsions (Z01EM134, Z06EM048, Z06EM050 and Z06EM053; see composition in previous examples) after multiples daily ocular topical administrations for 28 consecutive days into the right eye of albino rabbits.

Methods:
Ten (10) New Zealand White albino rabbits per group (5 males and 5 females) were involved in this study. Treatments (50 μl ocular topical administrations) were given four times a day for 28 consecutive days. General tolerance (body weight, food and water consumptions, general aspect, clinical signs, hematology and blood biochemistry), ocular tolerance (observations with an ophthalmoscope, slit lamp examinations and ocular histology) and necropsy (gross macroscopic examination, main organ weights) were investigated. A statistical analysis (MANOVA LSD test) was also performed on body and organ weights, on food and water consumption data, and on hematological and biochemical parameters Results:
General behaviour, food consumption and water consumption, body weight, organ weights were unaffected by treatments. There were no remarkable observations at necropsy due to treatment. Ophthalmological observations and microscopic examinations of the eyes and adnexa revealed no adverse effects. Ocular reactions were confined to slight conjunctival redness that were observed in all animals in the study and are commonly observed in rabbits after multiple instillations of ophthalmic products

The invention claimed is:
1. An ophthalmic oil-in-water submicron emulsion, which comprises colloid particles having an oily core surrounded by an interfacial film, said emulsion comprising:

1% by weight of mineral oil;
0.002% by weight of at least one cationic agent, said agent being cetalkonium halide;
0.3% by weight of tyloxapol; and
0.1% by weight of poloxamer,
wherein,
said emulsion does not contain phospholipids,
said emulsion does not contain anionic surfactants,
said emulsion has a positive zeta potential, and
said emulsion meets the zeta potential stability under thermal stress conditions as determined by Test A:
measuring zeta potential, in mV, of said emulsion at the time of preparation is $Z_0$,
sealing 5-10 ml of said emulsion in 10 ml Type I glass vials under nitrogen atmosphere without bubbling,
storing said sealed vials at 80° C. for 15 hours,
measuring zeta potential, in mV, of said emulsion at 15 hours, $Z_{15}$,
determining the difference between $Z_{15h}-Z_0$, $\delta A$, wherein, the emulsion meets the zeta potential stability under thermal stress conditions according to Test A for a $\delta A$ less than the standard error of zeta potential measurement.

2. The ophthalmic emulsion according to claim 1, which meets the zeta potential stability as determined by Test B:
measuring zeta potential, in mV, of said emulsion at the time of preparation is $Z_0$,
sealing 5-10 ml of said emulsion in 10 ml Type I glass vials under nitrogen atmosphere without bubbling,
storing said sealed vials at 80° C. for 48 hours,
measuring zeta potential, in mV, of said emulsion at 48 hours, $Z_2$,
determining the difference between $Z_2-Z_0$, $\delta A$, wherein, the emulsion meets the zeta potential stability under thermal stress conditions according to Test B for a $\delta A$ less than the standard error of zeta potential measurement.

3. The ophthalmic emulsion according to claim 1, which meets the zeta potential stability as determined by Test C:
measuring zeta potential, in mV, of said emulsion at the time of preparation is $Z_0$,
sealing 5-10 ml of said emulsion in 10 ml Type I glass vials under nitrogen atmosphere without bubbling,
storing said sealed vials at 80° C. for 7 days,
measuring zeta potential, in mV, of said emulsion at 7 days, $Z_7$,
determining the difference between $Z_7-Z_0$, $\delta A$, wherein, the emulsion meets the zeta potential stability under thermal stress conditions according to Test C for a $\delta A$ less than the standard error of zeta potential measurement.

4. The ophthalmic emulsion according to claim 1, which meets the zeta potential stability as determined by Test D:
measuring zeta potential, in mV, of said emulsion at the time of preparation is $Z_0$,
sealing 5-10 ml of said emulsion in 10 ml Type I glass vials under nitrogen atmosphere without bubbling,
storing said sealed vials at 80° C. for 14 days,
measuring zeta potential, in mV, of said emulsion at 14 days, $Z_{14}$,
determining the difference between $Z_{14}-Z_0$, $\delta A$, wherein, the emulsion meets the zeta potential stability under thermal stress conditions according to Test D for a $\delta A$ less than the standard error of zeta potential measurement.

5. The ophthalmic oil-in-water emulsion according to claim 1, further comprising a biguanide salt selected from the group consisting of chlorhexidine and salts thereof, polyaminopropyl biguanide, phenformin, alkylbiguanide and a mixture of two or more thereof.

6. The ophthalmic emulsion according to claim 1, further comprising a cationic agent selected from the group consisting of benzalkonium chloride, lauralkonium chloride, benzododecinium bromide, benzethenium chloride, hexacdecyltrimethylammonium bromide, tetradecyltrimethylammonium bromide, dodecyltrimethylammonium bromide and a mixture of two or more thereof.

7. The ophthalmic emulsion according to claim 1, wherein the cationic agent is selected from the group consisting of chitosan, 1,2-dioleyl-3-trimethylammonium-propane, 1,2-dioleoyl-sn-glycero-phosphatidylethanolamine, cationic glycosphingo-lipids or cationic cholesterol derivatives, and mixtures of two or more thereof.

8. The ophthalmic emulsion according to claim 1, further comprising benzalkonium chloride as a cationic agent.

9. The ophthalmic emulsion according to claim 1, wherein said colloidal particles have an average particle size of equal or less than 1 μm.

10. The ophthalmic emulsion according to claim 1, comprising a pharmaceutically active substance.

11. The ophthalmic emulsion according to claim 10, wherein the active substance is selected from the group consisting of antibiotics, antifungals, antibacterials, antivirals, anti-infection, anti-microbial drugs, antiallergenic, antiproliferative agents, synthetic glucocorticoids, mineralcerticoid, hormone forms deriving from the cholesterol metabolism, anti-inflammatory, antineoplastic, immunological drugs, insulin, calcitonin, parathyroid hormone and peptide, vaseppressin hypothalamus releasing factor, beta adrenergic blockers, cytokines, interleukins, growth factors, antibodies or antibody fragments, oligoaptamers, aptamers, immunosuppressant, immunomodulators, antithroinbolytic, vasodilator agents, antioxidants, and optically acceptable salts thereof.

12. The ophthalmic emulsion according to claim 10, wherein the active substance is an immunosuppressive agent selected from the group consisting of cyclosporine, sirolimus and tacrolimus.

13. The ophthalmic emulsion according to claim 12, wherein the active substance is cyclosporin A.

14. A process of preparation of a submicron ophthalmic oil-in-water type emulsion according to claim 1, comprising the steps of shear mixing followed by high pressure homogenization of the coarse emulsions obtained through mixing of the aqueous and the oily phase.

15. An ophthalmic formulation comprising a submicron emulsion according to claim 1, in combination with an ophthalmic acceptable carrier, said formulation being in the form of eye drops, eye ointment, or ophthalmic gel.

16. The ophthalmic formulation according to claim 15, comprising a pharmaceutically effective amount of an active ingredient in or within the ophthalmic acceptable carrier.

17. A delivery device selected from the group consisting of lenses, ocular patch, implant, and insert, said device containing an emulsion according to claim 1.

18. The ophthalmic oil-in-water emulsion according to claim 1, wherein the halide is chloride or bromide.

19. The ophthalmic oil-in-water emulsion according to claim 18, wherein the halide is chloride.

* * * * *

UNITED STATES PATENT AND TRADEMARK OFFICE
CERTIFICATE OF CORRECTION

PATENT NO. : 8,372,434 B2  Page 1 of 1
APPLICATION NO. : 11/667355
DATED : February 12, 2013
INVENTOR(S) : Bague et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1259 days.

Signed and Sealed this
First Day of September, 2015

Michelle K. Lee
*Director of the United States Patent and Trademark Office*